US009255263B2

(12) United States Patent
Smith et al.

(10) Patent No.: US 9,255,263 B2
(45) Date of Patent: Feb. 9, 2016

(54) ANTITHROMBOTIC COMPOUNDS

(75) Inventors: Richard Anthony Godwin Smith, London (GB); Steven Howard Sacks, London (GB); Anthony Dorling, London (GB)

(73) Assignees: King's College London, London (GB); Imperial Innovations Limited, London (GB)

( * ) Notice: Subject to any disclaimer, the term of this patent is extended or adjusted under 35 U.S.C. 154(b) by 0 days.

(21) Appl. No.: 13/394,177

(22) PCT Filed: Sep. 6, 2010

(86) PCT No.: PCT/GB2010/051478
§ 371 (c)(1),
(2), (4) Date: May 21, 2012

(87) PCT Pub. No.: WO2011/027175
PCT Pub. Date: Mar. 10, 2011

(65) Prior Publication Data
US 2012/0232014 A1 Sep. 13, 2012

(30) Foreign Application Priority Data
Sep. 4, 2009 (GB) .................................. 0915519.3

(51) Int. Cl.
| C07K 14/745 | (2006.01) |
| C12N 5/071 | (2010.01) |
| C12N 9/96 | (2006.01) |
| A61K 38/00 | (2006.01) |
| C07K 14/81 | (2006.01) |
| C07K 14/815 | (2006.01) |

(52) U.S. Cl.
CPC . *C12N 9/96* (2013.01); *A61K 38/00* (2013.01); *C07K 14/811* (2013.01); *C07K 14/815* (2013.01); *C07K 2319/033* (2013.01)

(58) Field of Classification Search
None
See application file for complete search history.

(56) References Cited

U.S. PATENT DOCUMENTS

2006/0241048 A1 10/2006 Esser et al.

FOREIGN PATENT DOCUMENTS

| WO | 90-03391 | 4/1990 |
| WO | 98-02454 A2 | 1/1998 |
| WO | 98-42850 A1 | 10/1998 |
| WO | WO 98/42850 | * 10/1998 |

OTHER PUBLICATIONS

Resh MD. Biochimica et Biophysica Acta. 1451;1-16:1999.*
Hirsh et al., Aterioscler Thromb Vas Biol. 21;1094-1096:2001.*
Schmitz et al. Eur J Biochem. 195;251-256:1991.*
Tamm eta l. Bioscience Reports. vol. 20, No. 6:2000.*
De Paula, Daniel et al, "Hydrophobization and bioconjugation for enhanced siRNA delivery and targeting," RNA (New York. N.Y.). vol. 13. No. 4. Apr. 2007. pp. 431-456.
Romberg, Birgit, et al., "Sheddable coatings for long-circulating nanoparticles," Pharmaceutical Research, vol. 25. No. 1. Jan. 2008, pp. 55-71.
Zhang Chuan-Ling et al, "Research progress in hirudin fusion protein—review—Abstract," Database accession No. NLM17490558, Journal of Experimental Hematology I Chinese Association of Pathophysiology Feb. 2007 LNKD-PUBMED:17490558. vol. 15. No. 1., pp. 215-218.
Poschel Katrin Annett et al, "Anticoagulant efficacy of PEG-Hirudin in patients on maintenance hemodialysis," Kidney International, vol. 65. No. 2. Feb. 2004, pp. 666-674.
International Search Report mailed Sep. 2, 20122 in Application No. PCT/GB2010/051478.
Hill et al., "Protection of erythrocytes from human complement-mediated lysis by membrane-targetted recombinant soluble CD59: a new approach to PNH therapy," Blood, 107(5), 2131-2137, 2006.

* cited by examiner

Primary Examiner — Amber D Steele
Assistant Examiner — Schuyler Milton
(74) Attorney, Agent, or Firm — Banner & Witcoff, Ltd.

(57) ABSTRACT

A soluble compound for preventing or reducing blood coagulation comprising an antithrombotic agent and a membrane binding element, wherein the antithrombotic agent has a weight of less than about 5,000 daltons. Also disclosed is a soluble compound for preventing or reducing blood coagulation comprising an anticoagulant joined to a membrane binding element via a joining element, wherein the joining element between the anticoagulant and the membrane binding element is less than about 10,000 daltons in weight. These compounds can be used in therapy and, in particular, in preventing or reducing blood coagulation. As a result, a method of treatment is provided comprising administering an effective amount of the compounds to a subject to prevent or reduce blood coagulation as well as a method of perfusing an organ, tissue or cell comprising contacting the compounds with the organ, tissue or cell to prevent or reduce blood coagulation. Also disclosed is an organ, tissue or cell which has been perfused with the compounds.

15 Claims, 8 Drawing Sheets

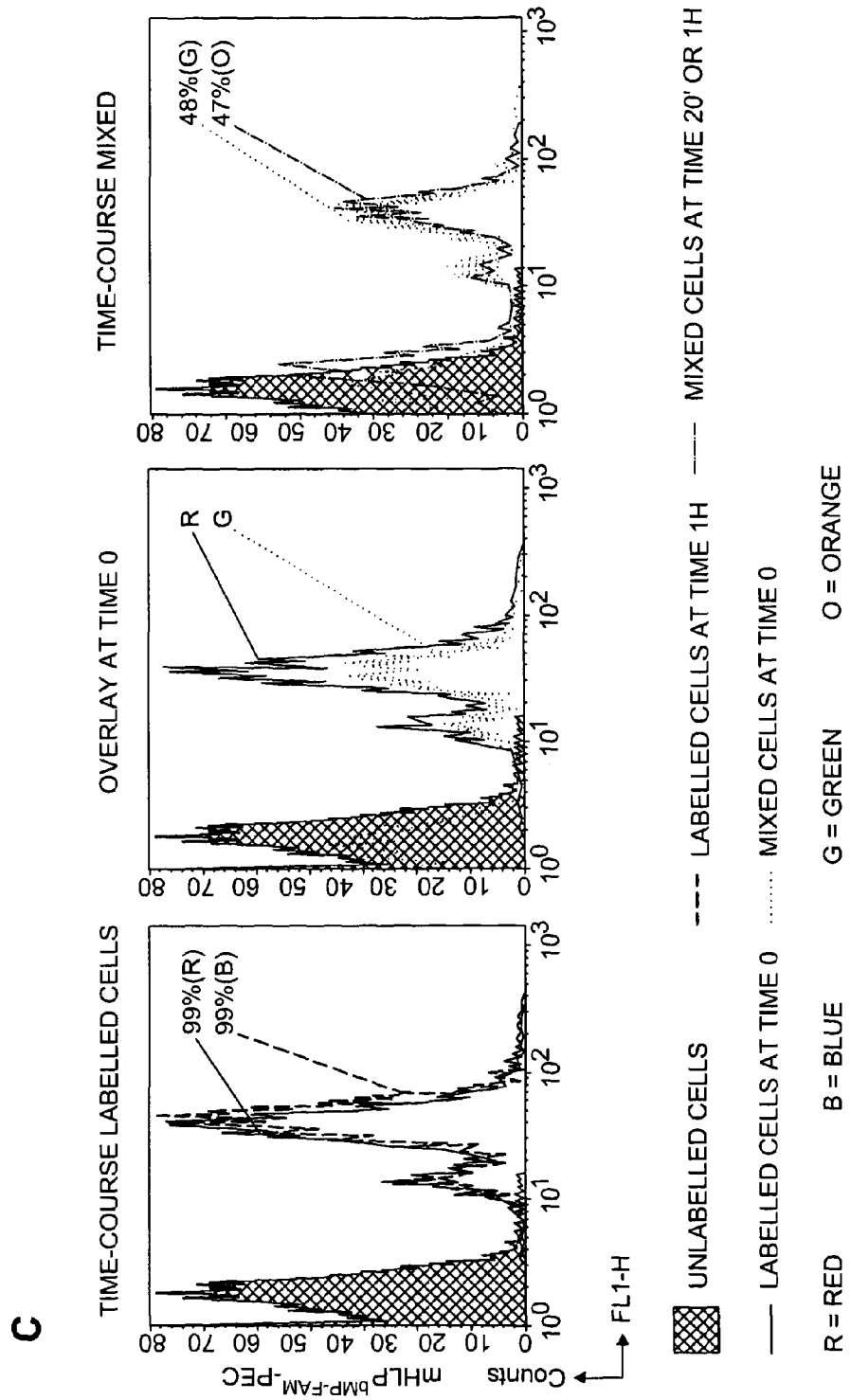

SEQUENCE LISTING

```
<160> NUMBER OF SEQ ID NOS: 5

<210> SEQ ID NO 1
<211> LENGTH: 9
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (2)..(3)
<223> OTHER INFORMATION: Xaa represents cyclohexylalanine

<400> SEQUENCE: 1

Phe Xaa Xaa Arg Lys Pro Asn Asp Lys
1               5

<210> SEQ ID NO 2
<211> LENGTH: 23
<212> TYPE: PRT
<213> ORGANISM: Artificial sequence
<220> FEATURE:
<223> OTHER INFORMATION: Synthetic construct

<400> SEQUENCE: 2

Phe Pro Arg Pro Gly Gly Gly Gly Asp Gly Asp Phe Glu Glu Ile Pro
1               5                   10                  15

Glu Glu Tyr Leu Gly Gly Cys
            20

<210> SEQ ID NO 3
<211> LENGTH: 16
<212> TYPE: PRT
<213> ORGANISM: Artificial sequence
<220> FEATURE:
<223> OTHER INFORMATION: Synthetic construct

<400> SEQUENCE: 3

Ser Ser Lys Ser Pro Ser Lys Lys Asp Asp Lys Lys Pro Gly Asp Cys
1               5                   10                  15

<210> SEQ ID NO 4
<211> LENGTH: 17
<212> TYPE: PRT
<213> ORGANISM: Artificial sequence
<220> FEATURE:
<223> OTHER INFORMATION: Synthetic construct

<400> SEQUENCE: 4

Gly Ser Ser Lys Ser Pro Ser Lys Lys Lys Lys Lys Lys Pro Gly Asp
1               5                   10                  15

Cys

<210> SEQ ID NO 5
<211> LENGTH: 9
<212> TYPE: PRT
<213> ORGANISM: Artificial sequence
```

```
<220> FEATURE:
<223> OTHER INFORMATION: Synthetic construct
<220> FEATURE:
<221> NAME/KEY: misc_feature
<222> LOCATION: (2)..(3)
<223> OTHER INFORMATION: Xaa represents cyclohexylalanine

<400> SEQUENCE: 5

Phe Xaa Xaa Arg Lys Pro Asn Asp Lys
1               5
```

ANTITHROMBOTIC COMPOUNDS

The present invention relates to therapeutic compounds and methods which enable the prevention, treatment and/or control of procoagulant or prothrombotic states. In particular, the present invention relates to the local prevention, treatment and/or control of procoagulant or prothrombotic states at the surface of cells, within organs or at sites of disease in humans and/or animals.

Materials that inhibit blood coagulation are well known in biochemistry and in clinical medicine. These materials (typified by heparin and Warfarin) act in the fluid phase to inhibit one or more steps in the coagulation cascade. Heparin acts as a cofactor for the plasma protein Antithrombin-III (ATIII) to inactivate thrombin (Factor IIa) and other proteases involved in coagulation. Warfarin acts upon the biosynthesis of coagulation factors whose active forms require Vitamin K-dependent gamma-carboxylation, and results in defective coagulation components and an inactive clotting cascade. In recent years, a variety of synthetic enzyme inhibitors have been derived by rational design based on the biochemistry and structural biology of the coagulation enzymes and their substrates. Anticoagulant agents have been reviewed by Kwaan & Samama (*Exp. Rev. Cardiovasc. Therapy,* 2, 511-22, 2004). All these agents have in common the property that they are administered systemically (intravenously, intramuscularly or orally) and their efficacy is predicated on their concentration in the blood or other body fluids. It is this fact that gives rise to the major clinical problem with anticoagulant therapy—bleeding. Haemorrhage arises from antithrombotic activity in the wrong place, that is, an effective inhibition of coagulation by a systemically administered dose of an agent acting at a biological site where an ongoing prothrombotic stimulus is required to maintain haemostasis. There are many situations where a powerful antithrombotic action is required at one site but this is incompatible with the avoidance of haemorrhage in many others. This situation can occur in transplantation and particularly in xenotransplantation where grafts can be highly prothrombotic because of a combination of upregulation of procoagulant proteins such as tissue factor and the absence or loss of coagulation control proteins such as ATIII bound to the glycosaminoglycan matrix of the outer cell layer.

Riesbeck et al. (*Circulation,* 98: 2744-52, 1998) and Chen et al. (*Am. J. Transplant.* 4: 1958-63, 2004), have addressed this problem by expression of known anticoagulant proteins (TFPI and Hirudin) as fusion proteins on the surface of cells including progenitor cells. This approach is also described in U.S. Pat. No. 6,423,316 which discloses fusions of anticoagulant proteins with significant portions of the CD4 molecule resulting in hybrid proteins containing at least 300 amino acids with inter-domain linkers to ensure flexibility. Such constructs restrict the presentation of antithrombotic activity to the cell surface but the approach requires engineering of the cells or the generation of transgenic animals (see also PCT application WO 98/42850).

WO 98/02454 provides soluble derivatives of soluble polypeptides in which the derivatives comprise two or more heterologous membrane binding elements of low membrane affinity which are covalently attached to the polypeptide so that the elements can interact independently and with additive affinity with different components of the outer cell membrane. WO 98/02454 also describes conjugates with protein agents which have autonomous functions when presented on the surface of cells. Some of the soluble derivatives of WO 98/02454 comprise anticomplement proteins. However, WO 98/02454 does not disclose the use of anticoagulant proteins.

The inventors have now identified relatively low molecular weight agents which can be manufactured by pharmaceutically acceptable processes, can function as membrane-bound antithrombotic agents and which can be applied therapeutically, thereby avoiding gene therapy.

Accordingly, in a first aspect, the present invention provides a soluble compound for preventing or reducing blood coagulation comprising an antithrombotic agent and a membrane binding element, wherein the antithrombotic agent has a weight of less than about 5,000 daltons.

The compound of the invention can bind to the cell membrane of cells, tissues and organs to prevent or reduce the formation of blood clots. Since the compound can bind to cell membranes, it can be administered locally so that the compound has an effect at a specific location rather than having a systemic effect. The compound can be used in the short-term manipulation of organs in transplantation. It can also be used in cell therapies in which it is desirable to confer resistance to coagulation.

An advantage provided by the compound is that it is relatively small and so it is relatively easy to manufacture. Further, the compound can be manufactured synthetically.

Previously, it was thought that the use of a relatively low molecular weight antithrombotic agent would not provide the desired effect. This is because, in general, small molecules, when attached to a cell surface, are rapidly internalised. For example, it is known that phospholipids, when labelled with various fluorescent dyes, are taken up into mammalian cells within a few minutes (e.g Moumtzi A et al., *J. Lipid Research,* 48, 565-82, 2007). Therefore, it was thought that a relatively low molecular weight antithrombotic agent would rapidly be taken into the cell so that it would not remain on the surface of the cell. Therefore, the antithrombotic agent would not be able to function effectively at the surface of the cell. Surprisingly, the inventors have found that when a relatively low molecular weight antithrombotic agent is used, it remains on the surface of the cell for a sufficient period of time so that it can provide the desired effect of preventing or reducing blood coagulation at the surface of the cell.

Further, low molecular weight antithrombotic agents are relatively small in size. This means that they are generally less immunogenic than larger agents, especially if they originate from an exogenous source.

The antithrombotic agent can be any suitable antithrombotic agent which is less than about 5000 daltons in weight. Such antithrombotic agents are well known to those skilled in the art. For example, the hirudin-derived peptide bivalirudin (Maraganore J. M. et al. *Biochemistry.* 29 (30), 7095-7101, 1990), the dipeptide boronates (e.g. Taparelli C. et al., *J. Biol. Chem.,* 268, 4734-41, 1993) and the arginine analogue argatroban (Okamoto S, *Biochem. Biophys. Res. Commun.* 101, 440-6, 1981) all have molecular weights well below 5 kilodaltons. The antithrombotic agent may be a peptide or small protein, or may be non-peptidic. Preferably, the antithrombotic agent is capable of inhibiting either thrombin or upstream components of the coagulation system. Preferably, the antithrombotic agent is an anticoagulant. Anticoagulants are agents which limit or prevent the conversion of fibrinogen to fibrin and the consequent formation of a clot. Antithrombotic agents also include agents which can prevent activation or aggregation of platelets. In one embodiment, the antithrombotic agent is an inhibitor or antagonist of the coagulation system (coagulation cascade). The antithrombotic agent may act on an enzymatic or non-enzymatic component of the coagulation system. The antithrombotic agent may be selected from the group consisting of inhibitors of serine proteases, such as HLL-1; antagonists of the protease-activated receptors (e.g. PAR-1, PAR-3 and PAR-4), such as 3-mercaptopropionyl-Phe-Cha-Cha-Arg-Lys-Pro-Asn-Asp-Lys-NH2 (which is an antagonist of PAR-1) (this antagonist contains SEQ ID NO. 1); peptide phosphonates and boronates; hirudin-derived peptides, such as bivalirudin; and arginine/amidinophenylalanine analogues of argatroban and NAPAP (Wagner G, Voight B & Vieweg H, *Pharmazie.*, 39,226-30, 1984). Preferably, the serine proteases are involved in the coagulation cascade. In one embodiment, the antithrombotic is an inhibitor of human thrombin (Factor IIa), human Factor Xa, human Factor IXa, human Factor XIa, human Factor XIIa, human kallikrein, human Factor VIIa or human Factor XIIIa. These factors are components of the coagulation cascade. In one embodiment, the antithrombotic agent is synthetic.

The antithrombotic agent is less than about 5,000 daltons in weight. Surprisingly, it has been found that such low molecular weight agents are not rapidly internalised by cells. The antithrombotic agent may be less than 4,500 Da, less than 4,000 Da, less than 3,500 Da, less than 3,000 Da, less than 2,500 Da, less than 2,000 Da, less than 1,500 Da, less than 1,000 Da, or less than 500 Da.

The membrane binding element may be any suitable molecule which is capable of binding to a cell membrane. Suitable naturally-occurring membrane binding elements are well known to those skilled in the art, either as components of proteins that mediate membrane interactions or as membrane components such as sterols or sphingolipids. For example, the membrane-interactive unit in the developmental protein SONIC HEDGEHOG comprises a cholesterol molecule linked to an N-terminal cysteine which acts in concert with a nearby upstream amino acid sequence (Pepinsky R B et al., *J. Biol. Chem.* 273, 14037-45, 1998).

The membrane binding element can bind to the membrane surface of a cell so as to localise the antithrombotic agent upon the external surface of the cell in a manner that permits the functionality of the antithrombotic agent to be expressed against its target. The membrane binding element should be sufficiently hydrophilic so that the compound of the invention is soluble.

The membrane binding element is preferably selected from: fatty acid derivatives such as fatty acyl groups; basic amino acid sequences; ligands of known integral membrane proteins; sequences derived from the complementarity-determining region of monoclonal antibodies raised against epitopes of membrane proteins; and membrane binding sequences identified through screening of random chemical or peptide libraries.

In one embodiment, the membrane binding element may be a phospholipid which has been derivatised to increase its water-solubility. For example, the phospholipid may be derivatised with a hydrophilic polymer, such as polyethylene glycol (PEG), polyvinylpyrrolidone, dextran, or polysarcosine. Other suitable polymers would be apparent to a skilled person.

The membrane binding element may be a glycosylphosphatidylinositol (GPI) anchor or an analogue thereof. Suitable GPI anchors and analogues are well known to those skilled in the art and are described, for example, in Paulick M G and Bertozzi C R (*Biochemistry* 47: 6991-7000, 2008). The carbohydrate portion of the GPI anchor may be comprised of any suitable saccharide monomers. Suitable saccharide monomers will be apparent to one skilled in the art as will the length of the carbohydrate portion.

In an alternative embodiment, the membrane binding element may be a peptide which is capable of interacting with one or more components of the outer cell membranes of cells, for example, phospholipids. Preferably, the peptide is between 3 and 25 amino acids. More preferably, the peptide is between 4 and 20 amino acids. Preferably, the peptide is a hydrophilic peptide. In one embodiment, the peptide comprises between three and 8 lysine residues, preferably, L-lysine residues.

The peptide may additionally comprise one or more groups which are capable of interacting with the lipid bilayer core of a cell membrane. Suitable groups are well known to those skilled in the art. These groups should be hydrophobic groups. For example, the one or more groups may be fatty acyl groups, such as myristoyl and/or palmitoyl groups. Preferably, the one or more groups are located at or near the N-terminal of the peptide. Other examples of suitable hydrophobic groups include long-chain aliphatic amines and thiols, steroid and farnesyl derivatives. This approach is based on the structure and function of the myristoyl-electrostatic switch (MES) (Thelen M et al. *Nature* 351: 320-2, 1991). In one embodiment, the one or more group is an isoprenoid group such as farnesyl and geranylgeranyl residues. The membrane binding element may be a plurality of groups which are capable of interacting with the lipid bilayer core of a cell membrane.

In another embodiment, the membrane binding element may be one or more groups which are capable of interacting with the lipid bilayer core of a cell membrane. These groups should be hydrophobic groups. The one or more groups may be fatty acyl groups, such as myristoyl, palmitoyl, or stearoyl groups. Other examples of suitable hydrophobic groups include long-chain aliphatic amines and thiols, steroids and farnesyl derivatives. In one embodiment, the one or more group is an isoprenoid group such as farnesyl and geranylgeranyl residues. The membrane binding element may be a plurality of groups which are capable of interacting with the lipid bilayer core of a cell membrane.

The compound of the invention may comprise one or more membrane binding elements. Preferably, the compound comprises one membrane binding element.

The antithrombotic agent and the membrane binding element of the compound are joined together. Preferably, the antithrombotic agent and the membrane binding element are joined covalently. The antithrombotic agent and the membrane binding element may be joined to each other directly. For example, they may be joined by a disulphide bond in which a free thiol group in one component reacts with a thiol-reactive group in the other component. If the antithrombotic agent is a protein, the join may be formed through a cysteine residue on the protein. Alternatively, the antithrombotic agent and the membrane binding element may be joined indirectly. For example, there may be a linker between the two components. The linker may be a homo- or hetero-bifunctional linker wherein one end of the linker is joined to one of the components and the other end of the linker is joined to the other component. The linker may be, for example, a hydrophilic polymer such as polyethylene glycol (PEG). Suitable linkers are well known to those skilled in the art.

The compound of the invention is soluble. Preferably, the compound is soluble in an aqueous solution so that it can be administered in solution at an effective concentration. Preferably, the compound is soluble enough so that it does not precipitate or form aggregates in solution.

In a second aspect, the present invention provides a soluble compound for preventing or reducing blood coagulation comprising an anticoagulant joined to a membrane binding element via a joining element, wherein the joining element between the anticoagulant and the membrane binding element is less than about 10,000 daltons in weight.

Due to the fact that the joining element of the compound has a relatively low molecular weight, it will be fairly small. Therefore, when the compound is bound to a membrane, the anticoagulant is held relatively close to the membrane. This allows, for example, a short linker to be used between the anticoagulant and the membrane binding element or, indeed, no linker at all. This makes the compound more simple which allows it to be produced more easily and more efficiently.

Surprisingly, the inventors have found that when the joining element between the anticoagulant and the membrane binding element is relatively short (i.e. it has a relatively low molecular weight), the anticoagulant can still function effectively. This is in spite of the fact that the anticoagulant is held relatively closely to the cell membrane when the compound is attached to a cell membrane. It would be expected that having a relatively short joining element would restrict the anticoagulant so that it would not be able to function effectively. This expectation derives from the fact that inhibition of the coagulation system is mainly mediated by interactions with the active centres of serine proteases which are typically located within pockets or clefts of the protein structure. A molecule designed to interact with such pockets would be expected to be sterically hindered from doing so if it was located on or close to a large membrane surface.

In WO 98/42850, a fragment of the CD4 protein is used to anchor agents to a membrane. However, domains 3 and 4 of the CD4 protein, which total about 200 amino acids in length (~25 kDa), are included. This means that two protein domains totaling about 200 amino acids are juxtaposed between the agent and the membrane. Additional linkers are also used to ensure the agents stay mobile and active. Therefore, the join between the agent and the portion of the molecule in the membrane is fairly long and, therefore, has quite a high molecular weight.

The 'joining element' between the anticoagulant and the membrane binding element in the present invention is the portion of the compound which connects the two functional components of the compound, these being the anticoagulant and the membrane binding element. Therefore, the anticoagulant component and the membrane binding element component are those parts of the compound which are involved in performing the relevant function. For example, if the membrane binding element included a section of polymer which was joined to the anticoagulant but which played no role in binding to the membrane, this portion of polymer would be consider to be a component of the 'joining element' between the two components rather than part of the membrane binding element.

The joining element may be formed by a linker which may be synthetic. The joining element may be formed by a protein linker or a non-protein linker, for example, a hydrophilic polymer such as polyethylene glycol (PEG). Alternatively, the joining element may simply be a chemical bond where the anticoagulant is joined directly to the membrane binding element.

In various embodiments, the joining element between the anticoagulant and the membrane binding element may be less than about 9,000 daltons in weight, less than about 8,000 daltons in weight, less than about 7,000 daltons in weight, less than about 6,000 daltons in weight, less than about 5,000 daltons in weight, less than about 4,000 daltons in weight, less than about 3,000 daltons in weight, less than about 2,000 daltons in weight, less than about 1,000 daltons in weight, less than about 750 daltons in weight, less than about 500 daltons in weight, or less than about 250 daltons in weight.

In one embodiment, the joining element between the anticoagulant and the membrane binding region is less than about 40 amino acids in distance. The term "40 amino acids in distance" means a distance which is equivalent to the length of 40 amino acids when in an extended (i.e. fully stretched) conformation. This is a distance of about 10 nm (assuming a single amino acid has a peptide bond length of about 0.25 nm). It does not mean that the joining element is formed of a peptide.

In various embodiments, the joining element between the anticoagulant and the membrane binding element may be less than about 35 amino acids in distance, less than about 30 amino acids in distance, less than about 25 amino acids in distance, less than about 20 amino acids in distance, less than about 15 amino acids in distance, less than about 10 amino acids in distance, or less than about 5 amino acids in distance. In one embodiment, the anticoagulant is covalently joined directly to the membrane binding element so that the length of the joining element is simply the length of one chemical bond.

In a particular embodiment, the anticoagulant is less than about 40 amino acids in distance from the membrane, when the compound is bound to a membrane. Alternatively, the anticoagulant may be less than about 35 amino acids in distance, less than about 30 amino acids in distance, less than about 25 amino acids in distance, less than about 20 amino acids in distance, less than about 15 amino acids in distance, less than about 10 amino acids in distance, or less than about 5 amino acids in distance from the membrane, when the compound is bound to a membrane.

The skilled person would easily be able to work out the distance of the joining element between the anticoagulant and the membrane binding element. For a simple chemical linker, the skilled person could calculate it mathematically by taking into account the bond lengths between the atoms, the identity of the atoms, etc. For a protein linker which may be in a folded conformation, the distance can be determined by measuring the cross sectional distance across the protein linker. This can be done by determining the structure of the protein linker (or the intact conjugate), for example, using x-ray crystallography or NMR spectroscopy.

The distance between the anticoagulant and the membrane surface when the compound is bound to a membrane may be estimated by fluorescence methods such as FRET (fluorescence resonance energy transfer). In this method, the interaction is measured between a fluorescent component of the anticoagulant such as a fluorescent dye or a tryptophan residue located at the distal part of this component and a fluorescent molecule such as pyrene which is effectively dissolved uniformly in the lipid bilayer (see for example, Qui L et al., *Biophys J.,* 96, 4299-307, 2009).

Preferably, the joining element is not formed by multiple protein domains.

Further features of the compound, the anticoagulant and the membrane binding element are as described above for the first aspect of the invention. However, it will be apparent to one skilled in the art that the anticoagulant does not have to be less than 5,000 daltons, although in some embodiments it may be.

The present invention also provides a pharmaceutical composition comprising the compound described above and one or more pharmaceutically acceptable excipients. Suitable pharmaceutical excipients are well known to those skilled in the art. Pharmaceutically acceptable excipients that may be used in the pharmaceutical composition of this invention include, but are not limited to serum proteins, such as human serum albumin, buffer substances such as phosphates, glycerine, sorbic acid, potassium sorbate, partial glyceride mixtures of saturated vegetable fatty acids, water, salts or electrolytes, disodium hydrogen phosphate, potassium hydrogen phosphate, sodium chloride.

When the pharmaceutical compositions of this invention are administered to a subject, they may be administered in any suitable way. Preferably, the composition is administered by injection, more preferably by local injection into an organ or a site of disease. The pharmaceutical compositions of this invention may contain any conventional non-toxic pharmaceutically-acceptable carriers or vehicles. The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant. It should be noted that if oil-in-water dispersions are employed, the compound of the invention is, by virtue of its hydrophobic components, likely to localise on the surface of the oil droplets. This may affect the rate at which the compounds transfer to the cell surface when the dispersion is contact with cells or the vasculature of an organ. Preferably, the compound is in an aqueous solution.

Other pharmaceutically acceptable additives which may be added to the composition are well known to those skilled in the art.

The present invention also provides the compound described above for use in therapy.

Further, the present invention provides the compound described above for use in preventing or reducing blood coagulation.

Additionally, the present invention provides the use of the compound described above in the preparation of a medicament for preventing or reducing blood coagulation.

Diseases and/or conditions which can be prevented, reduced and/or treated using the compound of the invention are myocardial infarction, stroke, arterial thrombosis, venous thrombosis, Budd-Chiari syndrome, Paget-Schroetter disease, thrombosis of the axillary-subclavian vein, pulmonary embolism and thrombosis associated with organ transplantation.

Local delivery of the compound of the invention to sites of potential thrombotic stimulus (such as angioplasty sites) in subjects can be carried out so as to retain some of the compound at the required site. This is in contrast to conventional antithrombotic agents whose local action will only be manifest as long as sufficient blood levels are maintained.

Therefore, the present invention provides a method of treatment comprising administering an effective amount of the compound described above to a subject to prevent or reduce blood coagulation.

The subject may be any suitable subject in need of prevention or reduction in blood coagulation. Preferably, the subject is a mammal More preferably, the subject is human.

The compound is preferably administered locally. The compound can be administered to the heart, liver, kidney, lungs, pancreas including pancreas islets, skin, corneum or sites of arthroplasty.

Acute myocardial infarction can be treated by administration of the compound of the invention. This can be through a balloon catheter during percutaneous transluminal angioplasty.

One embodiment of the invention is the use of the compound in perfusion/wash protocols in which the compound is passed through an organ to be transplanted under conditions that allow binding of the compound to the cells of the organ vasculature. Excess compound can be removed by washing of the vasculature.

The practical advantage of this approach is that it enables antithrombotic activity to be delivered selectively to perfused organs, to local sites in vivo and to the surface of isolated cell populations and to persist at those sites for moderate periods of time (hours to days). This effect has the potential to improve the transplantation of solid organs by reducing the acute prothrombotic effects of organ grafting.

In a further aspect, the invention provides for a method of treating an organ, tissue or cell in which the organ, tissue or cell is contacted with a solution of the compound in a physiologically acceptable perfusion medium prior to administration to the patient or transplantation. The contact time will depend on the organ or cell type to be modified but will typically be from a few minutes (cells in free suspension) to approximately one hour (larger solid organs). The excess compound can then be removed from the organ, tissue or cell by washing out with excess perfusion solution or by one or more cycles of cell isolation and washing without the added compound. This process can be applied to solid organ transplantation of the kidneys, heart, liver or pancreas as well as to transplanted tissues such as skin or corneum and to pancreatic islet cells. In addition, localisation of the antithrombotic activity can also be applied to cell therapy products. These applications include but are not limited to red blood cells (erythrocytes) or platelets for blood transfusion and to stem cells grown in culture for a wide variety of applications in regenerative medicine. In each case, a temporary ability to inhibit local thrombosis is conferred upon the cells. That antithrombotic effect has advantages in preventing acute loss of cell viability (such as occurs with transplanted pancreatic islets) and reducing the risk of cells being sequestered in unintended locations.

In a further aspect, the invention provides for a method of treating a thrombotic or potentially thrombotic disease by local administration of the compound into a specific body site at low doses and without a specific wash step. Such applications include administration into a temporarily isolated coronary artery segment during percutaneous transluminal coronary angioplasty or into an arthroplasty site during procedures such as hip replacement with a high attendant risk of thrombosis.

The present invention also provides the use of the compound for perfusing organs, tissues or cells.

Further, the present invention provides a method of perfusing an organ, tissue or cell comprising contacting the compound with the organ, tissue or cells to prevent or reduce blood coagulation.

More specifically, with regard to organ perfusion, the present invention provides a method of perfusing an organ comprising contacting the compound with the blood vessels of an organ so that the compound binds to the blood vessels of the organ in order to prevent or reduce blood coagulation in the organ.

The method can additionally comprise the step of washing the organ, tissue or cell. Cells can be washed by successive centrifugation and resuspension steps to remove compound not bound to the cell surface. Washing of an organ can be through repeat perfusion with a solution not containing the compound.

The compound can be administered in any suitable form. The compound is preferably in a solution and, more preferably, a physiologically acceptable solution.

The organ should be perfused for sufficiently long to ensure transfer of the compound to the vascular surface of the organ.

The cells that are perfused can be any suitable cells. In certain embodiments, the cells are derived from human blood, human embryonic or induced pluripotent stem cells, and may include erythrocytes, platelets, lymphocytes, fibroblasts, mesenchymal stem cells and endothelial, epithelial or stromal cells.

The organ can be any suitable organ, for example, the heart, liver, kidney, lungs, pancreas including pancreas islets, skin or corneum.

Additionally, the present invention provides an organ, tissue or cell which has been perfused with the compound.

The present invention will now be described in detail, by way of example only, with reference to the figures in which:

FIG. 1 shows the results of a cellular inhibition assay.

FIG. 2a shows the appearance of cells incubated for 5 and 10 minutes at 10 uM and 1 uM.

EXAMPLES

Example 1

Figure 1:
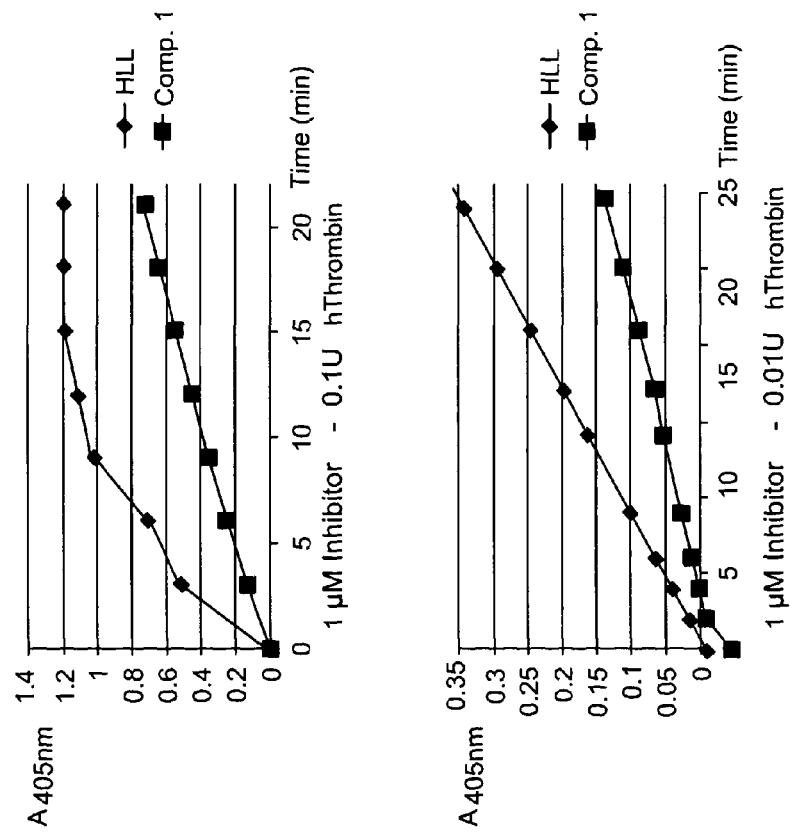
Figure 1:
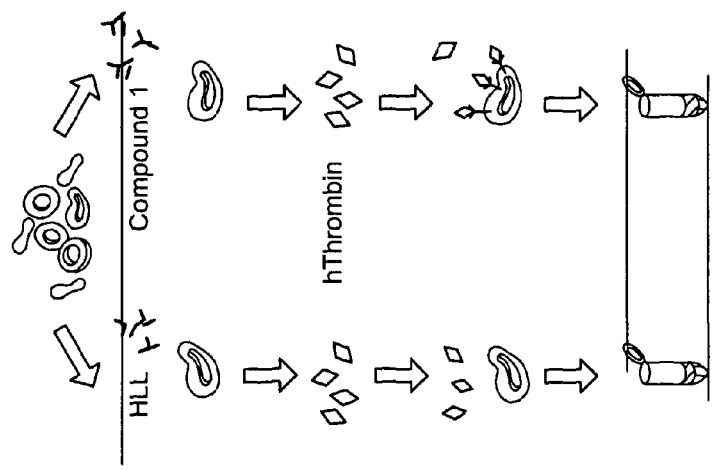

Conjugate of Anticoagulant Peptide HLL-1 with 1,2-distearoyl-sn-glycero-3-phosphoethanolamine-N-[2-thiopropionyl(polyethyleneglycol)-2000].
[Compound 1]

HLL-1 is H-dFPRPGGGGDGDFEEIPEEYLGGC-amide (SEQ ID NO. 2) in which all amino acids except the first are the L-configuration. This peptide was prepared by standard solid-phase peptide synthesis, purified by standard HPLC procedures and lyophilised as a white powder. Ellmans' titration of free thiol (Ellman G L, *Arch. Biochem. Biophys.* 82, 70-7, 1959) and elemental analysis showed that the lyophilised powder was approximately 70% peptide. The molecular weight of the peptide was found by mass spectrometry to be 2397.1 [M+H]+. The extinction coefficient of HLL-1 at 280 nm and 25° C. was found to be 1356 M−1 cm−1.

HLL-1 (12 mg, 3.28 micromoles) was dissolved in water (0.6 ml) and mixed with a solution of 1,2-distearoyl-sn-glycero-3-phosphoethanolamine-N-[PDP(polyethylene glycol)-2000] (Avanti Polar Lipids, Alabaster Ala., 10 mg, 3.3 micromoles) in 0.1M sodium chloride, 0.05M sodium phosphate pH 7.2 (PBS, 0.3 ml). Upon incubation at ambient temperature (~22° C.), the solution became cloudy but went almost clear when transferred to ice for 1 hour. The bulk of this solution (0.75 ml) was mixed with PBS (4.25 ml) and concentrated using a centrifugal concentration cartridge (Vivaspin V/S 6 PES, Sartorius-Stedim, Göttingen, Germany) with a nominal molecular weight cut-off of 5 kilodaltons. Concentration was performed at approximately 2500 RCF for 45 min at 20° C.) and the final volume was 1 ml. Three cycles of dilution/concentration were performed to yield a final volume of 1.25 ml containing approximately 2.1 mM Compound 1.

Experience with several batches of Compound 1 suggested that multiple cycles of ultrafiltration/concentration using membranes with a 5- or 3-kilodalton cutoff were the most effective way of separating the conjugate (Mr 5272 daltons) from its constituents. Separate experiments in which the release of pyridine-2-thione from the PDP functionality was monitored at 343 nm also indicated that the reaction of the components was rapid and went to completion. It was observed that when performed at room temperature, the coupling reaction was accompanied by the formation of a cloudy solution and a white precipitate and that this process was partly reversible by cooling to 0° C.

It was later found that both the solubility of the products in this coupling reaction and the efficiency of the coupling process were pH dependent. Improved yields were obtained if the pH of the HLL-1 solution was adjusted to between 7 and 8 (preferably around 7.6) using 10 mM sodium hydroxide. This is probably due to the fact that HLL-1 peptide, as prepared by solid-phase synthesis, contained significant amounts of trifluoracetic acid from the deprotection step. Further pH adjustment after addition of the tailing reagent was also found to be advantageous.

Polyacrylamide gel electrophoresis in the presence of sodium dodecyl sulphate (SDS-PAGE) was performed using 12% w/v Bis-Tris gels in MES running buffer (Invitrogen, Carlsbad, Calif.). In this system, HLL-1 migrated with an anomalously high apparent molecular weight (~6.5 kDa) whereas the PEG-phospholipid behaved normally (Mr ~3 kDa). Upon coupling, Compound 1 ran as a distinct band with Mr ~5 kDa. These results may be explained if HLL-1 migrates anomalously slowly on SDS-PAGE, due to its negatively charged nature which could discourage binding to SDS Linkage to the PEG lipid may then restore SDS binding.

Example 2

Conjugate of Anticoagulant Peptide HLL-1 with N-(α,ε bis-myristoyl lysine) SSKSPSKKDDKKPGDC-acid (containing SEQ ID NO. 3) [Compound 2]

N-(α,ε E bis-myristoyl lysine) SSKSPSKKDDKKPGDC-acid (containing SEQ ID NO. 3) (All-L, Hill A, Ridley S. H. et al., *Blood*, 107, 2131-2137, 2006) was prepared in the activated S-(2-pyridyl)thiocysteine form by solid phase synthesis. This compound has a molecular weight of 2365 daltons. HLL-1 peptide (3.5 mg 0.94 micromoles) was dissolved in PBS buffer (0.1 ml) and a solution of N-(α,ε bis-myristoyl lysine) SSKSPSKKDDKKPGDC(S-2-thiopyridyl)-OH (containing SEQ ID NO. 3) (5 mg, 0.932 micromoles thiol-equivalent) in dimethyl sulphoxide (DMSO, 0.1 ml) added. The mixture was held on ice for 3 h and then 100 ul fractionated on a Superdex 10/300GL peptide column (GE Healthcare, Uppsala, Sweden) at 22° C. using an AKTA purifier pump system (GE Healthcare, Sweden) in 0.02 mM sodium phosphate buffer pH 7.0 run at 0.5 ml/min. The product eluted in a UV-detectable peak at 8.1 ml and a pool between 7.8 and 8.5 ml was collected and stored at −80° C. Unreacted HLL-1 was detected at 12.5 ml and N-(α,ε bis-myristoyl lysine) SSKSPSKKDDKKPGDC(S-thiopyridyl)-OH (containing SEQ ID NO. 3) was observed at 10.5 ml. Larger amounts of this conjugate (Mr 4651 daltons) were also processed by the ultrafiltration method described in Example 1 using a 3 kilodalton cut-off membrane. pH adjustment as described for Example 1, was also found to be useful in this case.

Example 3

Conjugate of Anticoagulant Peptide HLL-1 with N-myristoyl-GSSKSPSKKKKKKPGDC(S-2-thiopyridyl)-amide (containing SEQ ID NO. 4) [Compound 3]

N-myristoyl-GSSKSPSKKKKKKPGDC(S-2-thiopyridyl)-amide (containing SEQ ID NO. 4) (Smith R, *Biochem. Soc. Transactions,* 30: 1037-41, 2002) was prepared by solid phase synthesis. 0.1 ml of a solution of this conjugate (10 mg/ml) in DMSO was added to a solution of HLL-1 in PBS (4.8 mM, 0.2 ml). The mixture was held at 24° C. for 1 h and the concentration of 2-thiopyridine released calculated from the absorbance at 343 nm. This indicated that only about 60% of the HLL-1 had reacted and a further 0.05 ml of the N-myristoyl-GSSKSPSKKKKKKPGDC(S-2-thiopyridyl)-amide (containing SEQ ID NO. 4) was added. After a further 30 min at 24° C., approximately 84% of the HLL peptide had reacted. The mixture was diluted to 2 ml with PBS (slight cloudiness was observed) and then concentrated using a Vivaspin 2 3 kDa cutoff PES membrane cartridge at 2500 rpm/4° C./90 min. The product was found to have only limited solubility in aqueous buffers and DMSO (>50% v/v) was needed to maintain solubility. Compound 3 has a theoretical molecular weight of 4403 daltons.

Example 4

Conjugate of N-(3-mercaptopropionyl)-F-Cha-Cha-RKPNDK-amide (containing SEQ ID NO. 5) with N-myristoyl-GSSKSPSKKKKKKPGDC(S-2-thiopyridyl)-amide (containing SEQ ID NO. 4) [Compound 4]

N-(3-mercaptopropionyl)-F-Cha-Cha-RKPNDK-amide (containing SEQ ID NO. 5 in which Cha represents cyclohexylalanine) (Mr 1297) was obtained from Peptides International, Louisville, Ky., USA. 54 Microliters of a 20 mg/ml solution in DMSO was added to 100 ul of a 20 mg/ml solution of N-myristoyl-GSSKSPSKKKKKKPGDC(S-2-thiopyridyl)-amide (containing SEQ ID NO. 4) in DMSO. Analysis of this material by SDS-PAGE (condition as in Example 1) showed that a product of apparent Mr ~4.5 kilodaltons formed in the reaction. This could be reduced by tris-(2-carboxyethyl)phosphine (TCEP) to products with the molecular weights of the components.

Example 5

Inhibitory Activity of Compounds 1 and 2 Against Human Thrombin in Free Solution $K_i$ of Compound 1 against human thrombin.

Materials: Human plasma thrombin (T6884) and N-p-Tosyl-Gly-Pro-Arg-p-nitroanilide (T1637) were obtained from Sigma-Aldrich (Gillingham, UK)

Assay: Thrombin-catalyzed hydrolysis of N-p-Tosyl-Gly-Pro-Arg-p-nitroanilide was monitored at 405 nm on a Spectramax Plus384 (Molecular Devices, Sunnyvale Calif., USA,). Stock solution of human plasma Thrombin and of substrate were prepared at concentrations of 10 U/mL and 1 mM, respectively, in 0.05M Tris-HCl, pH 7.5, 0.1 M NaCl and 0.5% BSA (Chung et al., *Analytical Biochem* 1985, 147, 49-56).

Reaction mixtures were prepared with buffer, thrombin (5 ul, 0.05 U) and substrate (100 ul, 125 nM) to a final volume of 800 ul and incubated at 25° C. When Inhibitor (PTL006 and HLL) was also included in the reaction mix, thrombin and inhibitor were premixed in the reaction cuvette at 25° C. for ~7 min and reaction was then initiated by addition of substrate. Substrate concentration and reaction mixture were as above.

The $K_M$ of thrombin for N-p-Tosyl-Gly-Pro-Arg-p-nitroanilide substrate was determined under these conditions. The velocity of thrombin-catalyzed reaction was plotted against substrate concentration values using GraphPadPrism5 software and fitting data with non-linear data matching option. For each substrate concentration assayed, the velocity of the enzyme reaction represented the slope of the linear phase, expressed as amount of product formed per time ($A_{405}$ vs time).

The $K_M$ of Thrombin for N-p-Tosyl-Gly-Pro-Arg-p-nitroanilide substrate was found to be 10.47±2 nM.

Using this $K_M$, the $K_i$ values of HLL and Compound 1 were determined using the same software as above. Velocity values of thrombin-catalyzed reaction were plotted against logarithm of inhibitor concentration and data fitted by non-linear regression and the one-site competitive binding equation option.

The $K_i$, values obtained were 1.99 nM for HLL and 2.85 nM for Compound 1 indicating that conjugated and unconjugated peptide had similar affinities for thrombin under these conditions.

Example 6

Inhibitory Activity of Compound 1 Bound to Guinea Pig Erythrocytes Against Exogenous Human Thrombin The assay and results with Compound 1 are shown schematically in FIG. 1:

Method and results. Guinea Pig Blood Cells (GPBC$_s$ Harlan, UK) were extensively washed with Gelatin Veronal Buffer (GVB, Sigma G6514). A fixed volume of cell suspension (100 ul containing about $10^8$ cells) was then diluted 1:1 with GVB before Compounds 1 or 2 were added; control HLL was used at the same final concentration. Cells were incubated for 10 min at ambient temperature with gentle agitation. Three washes with GVB were performed (each with at least 500 ul GVB) before discarding the supernatant and leaving cell pellet as dry as possible. Cell pellet was then resuspended with GVB and hThrombin (between 0.01 and 0.1 units) was added: reaction volume was 460 ul. Cells were incubated for 3 min at 37° C. in a waterbath and after incubation, gently pelleted by centrifugation. Supernatant (~400 ul) was recovered and spun again to remove any residual cells. Supernatant (380 ul) was transferred to a spectrophotometer and 70 l of GVB and 50 ul thrombin substrate (1 mM in GVB) added. The sample adsorbance was recorded at 405 nm for 20 min at 25° C.

The results shown in FIG. 1 demonstrate that GPBCs exposed to the same concentration of HLL and Compound 1 have differing effects on thrombin presented to them in free solution. Exposure to 1 uM Compound 1 resulted in ~60% inhibition of the activity of thrombin (relative to exposure to HLL) when thrombin was added at 0.1 units and >70% inhibition when 0.01 unit of thrombin was employed.

Example 7

Comparison of Compounds 1 and 2 Using the GPBC Assay

The cell-based thrombin inhibitory capacity of Compounds 1 and 2 were compared by normalising for cell number in the GPBC assay. The ratio Compound 2/Compound 1 for the specific cell inhibition capacity was found to be 2.1 when 0.05 U of thrombin was added to the cells and 1.3 when 0.1 U of thrombin was used. Both values result from using inhibitors at 1 uM final concentration of the compounds at the cell-binding step. Thus, Compound 2 appears to be somewhat more potent than Compound 1 in this assay.

Example 8

Inhibitory Activity of Compound 1 Against a Prothrombotic Cell Line Measured by a Whole Blood Coagulation Assay Human plasma preparation: Human blood was drawn from volunteers with heparin and human plasma prepared by centrifugation, before storage at −80° C.

Human plasma recalcification assay (based on Lin et al Transplantation, 86(5):702-9, 2008): Human CD34-derived progenitor cells were suspended in 50 µl Tris-buffered saline and mixed with 100 µl of normal human plasma (Sigma) in glass tubes (Corning, Corning, N.Y.). Ten (10) µl of 250 mM $CaCl_2$ in Tris-buffered saline combined with 90 µl phospholipids (Diagnostic Reagents, Oxford, UK) were added, and the tube incubated at 37° C. in a water bath—the time for a fibrin clot to form was determined in triplicate, during which time the tubes were continuously agitated by tilting. In some assays, cells were incubated with 200 uL of Compound 1 (50 uM) for 30 min at 4° C. before washing twice and inclusion in the clotting assay.

| Results (Example experiment, (values = seconds)) | | | |
| --- | --- | --- | --- |
| Condition | No Cells | Cells | Cells + C.1 |
| Tube 1 | 170 | 106 | 169 |
| Tube 2 | 191 | 110 | 172 |
| Tube 3 | 192 | 113 | 175 |
| Mean | 184.3 | 109.7 | 172 |
| SEM | 7.17 | 2.03 | 1.73 |

Conclusions:

CD34+ human progenitor cells promoted fibrin clot formation in re-calcified human plasma. Pre-incubating with Compound 1 inhibited this effect, but not the clotting initiated by the intrinsic pathway (glass tubes) indicating that the inhibitory effect was dependent on the presence of cell membranes. Control experiments with HLL (not shown) showed little inhibition of cell-mediated clotting indicating that this agent was removed during the wash steps.

Example 9

Preparation of FAM-Labelled Compound 1 [Compound 5]

HLL peptide and Compound 1 possess only one primary amino group which is located at the N-terminus of HLL. Therefore amine-reactive reagents will label both HLL and Compound 1 selectively at the N-terminus. The AnaTag™ 5-FAM protein labelling kit (72054, Cambridge Bioscience, Cambridge UK) was used to label Compound 1 with 5-FAM (5-carboxyfluorescein), which shares the same excitation and emission wavelengths as FITC but reacts with amine groups forming a carboxamide bond. Reaction conditions were those recommended by the manufacturer. Briefly, 200 ug Compound 1 were mixed with kit buffer B and reconstituted FAM in DMSO and shaken for 3 h at ambient temperature on a rotator. The reaction mixture was then purified by Vivaspin concentrators (3 kDa cutoff) which allowed buffer exchange at the same time. The physical and spectral properties of Compound 5 were as follows: Fluorescence: Green, Mr: 5745 Da, Absorbance maximum: ~495 nm, Emission maximum: ~520 nm.

Example 10

Binding of Compound 5 to Porcine Endothelial Cells

Figure 2A:
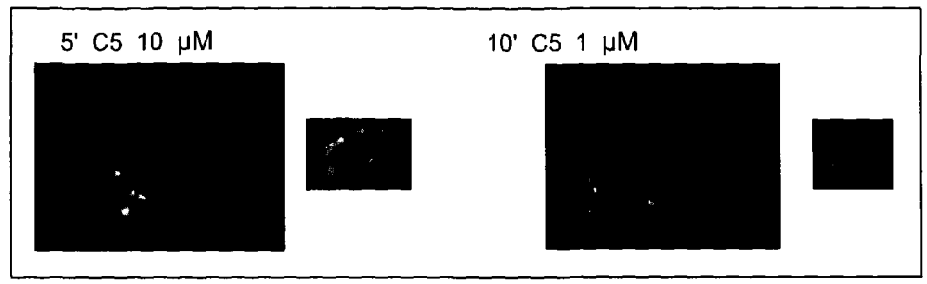
FIG. 2b shows FACS intensity distribution of A10 cells exposed to no compound no. 5, 0.1 uM, 1.0 uM and 10 uM. 5 min treatment. FL1-H Gated.
Figure 2B:
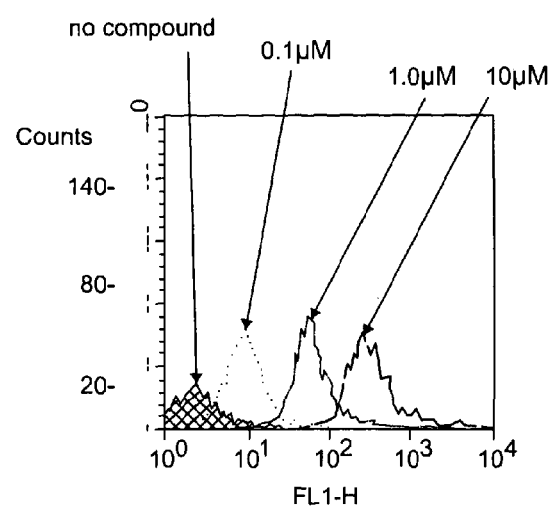

Porcine A10 endothelial cells (PEC) were grown in DMEM medium (Gibco) supplemented with 10% heat-inactivated fetal bovine serum, penicillin, streptomycin, and L-glutamine (complete medium, Hyclone, Fisher Scientific, UK). Cells were passaged every 2-3 days in 75-$cm^2$ flasks and maintained at 37° C. in an atmosphere of 5% $CO_2$ and 98% relative humidity. On the day of experiment, cells were treated with Trypsin-EDTA (Gibco) and washed in PBS, before being resuspended in 100 ml of Compound 5 (1 or 10 uM) for 5 min or 10 min (incubation was performed at ambient temperature). Thereafter cells were extensively washed 3 times with PBS before being analysed by FACScan (Becton Dickinson). Stringent sorting gates were set in order to exclude cellular debris and cellular clusters as well as the autofluorescence of non-transfected cells. About $10^5$ cells were collected for each observation. Data were processed by CELLQUEST software. The appearance of cells incubated for 5 and 10 minutes at 10 uM and 1 uM respectively is shown in FIG. 2a.

Both direct microscope observation and FACS analysis showed that Compound 5 interacted directly and in a dose-dependent fashion with A10 PEC cells when incubated for short periods of time at concentrations between 0.1 and 10 uM.

Example 11

Localisation of Compound 5 within the Rat Kidney Upon Perfusion

A seven week old (~250 g) male Dark Agouti (DA) rat was anaesthetised by inhalation of oxygen and isofluorane. A midline laparotomy was performed to facilitate the intrarenal delivery of agent. The perfusion of the DA kidney with the peptide involved the following steps:

The aorta was ligated above and below the renal pedicle;

A portex catheter, attached to a 3-way tap, was inserted between the ligatures and secured;

The renal vein was incised;

The kidney was perfused through the aorta with 5 ml of Soltran solution (Baxter, UK) containing Compound 5 at a concentration of 2 µM. Perfusion was for 5 min at a rate of 1 ml/min;

The agent was kept in contact with the kidney for 10 min; and

The kidney was flushed at the same rate with 5 ml of Soltran solution to get rid of any unbound material.

Figure 3:
FIG. 3 shows a florescence photomicrograph (×200) of compound no. 5 in a rat kidney section.

At that point the kidney was harvested and snap-frozen on liquid nitrogen. Sections were cut and allowed to dry in air for 30 min before adding PermaFluor aqueous mounting medium (LabVision, Fremont, Calif.). The sections, kept in the dark and at room temperature, were analysed under the microscope 15 min after. FIG. 3 shows the green FAM fluorescence of Compound 5 located in particular on the glomeruli of the kidney. This demonstrates that Compound 5 (and by inference Compound 1) can be delivered to critical areas of the kidney by a perfusion and washing protocol.

Example 12

Preparation of FAM-Labelled Compound 2 (Compound 6)

The procedure of Example 9 was employed except that HLL was first conjugated with 5-FAM and thereafter the membrane-anchoring tail N-(α,ε bis-myristoyl lysine) SSKSPSKKDDKKPGDC(S-2-thiopyridyl)-acid (containing SEQ ID NO. 3) was added followed by processing as in Example 9. This approach was necessary to ensure coupling with only one FAM molecule because the tail in this case contains several lysine residues. Compound 6 (Mr 5009 daltons) was observed to be slightly different in colour to Compound 5 despite a similar absorbance spectrum.

Example 13

Binding of FAM Derivatives of Compounds 1 and 2 (Compounds 5 and 6) to Red Blood Cells [FACS] and Measurement of Inter-Cell Transfer FACS experiments were performed as described in Example 5. Inter-cell transfer ("painting") experiments were performed by mixing labelled cells with same amount of unlabelled cells before analysis. The time elapsed between mixing and FACS analysis was kept to a minimum for initial analysis.

Figure 4A:
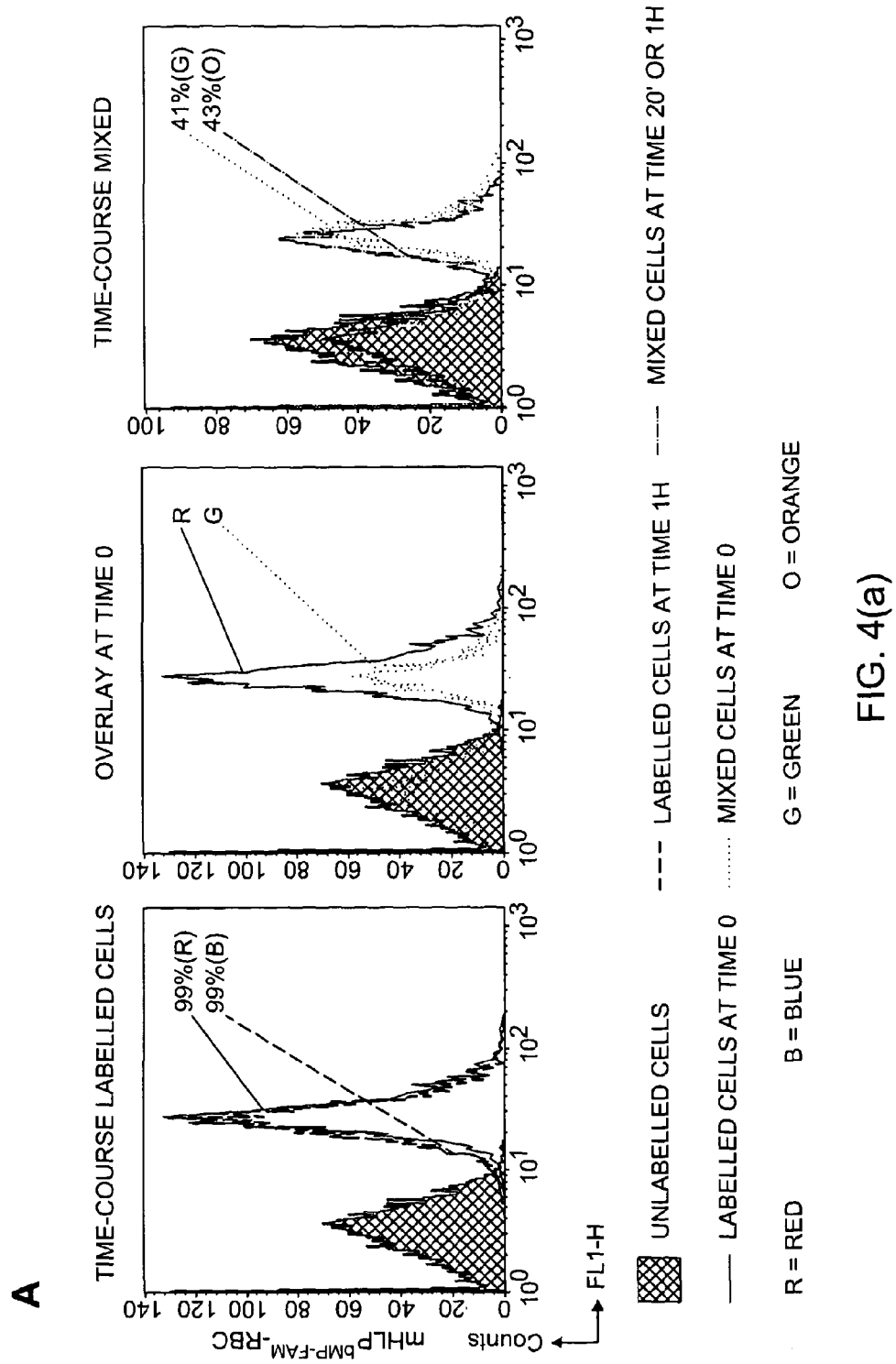
FIG. 4 shows FACS plots for Compound 5 (mHLP$^{PPE-FAM}$) and Compound 6 (mHLP$^{bMP-FAM}$) binding to red blood cells (panels A and B) and to PEC endothelial cells (panels C and D).
Figure 4B:
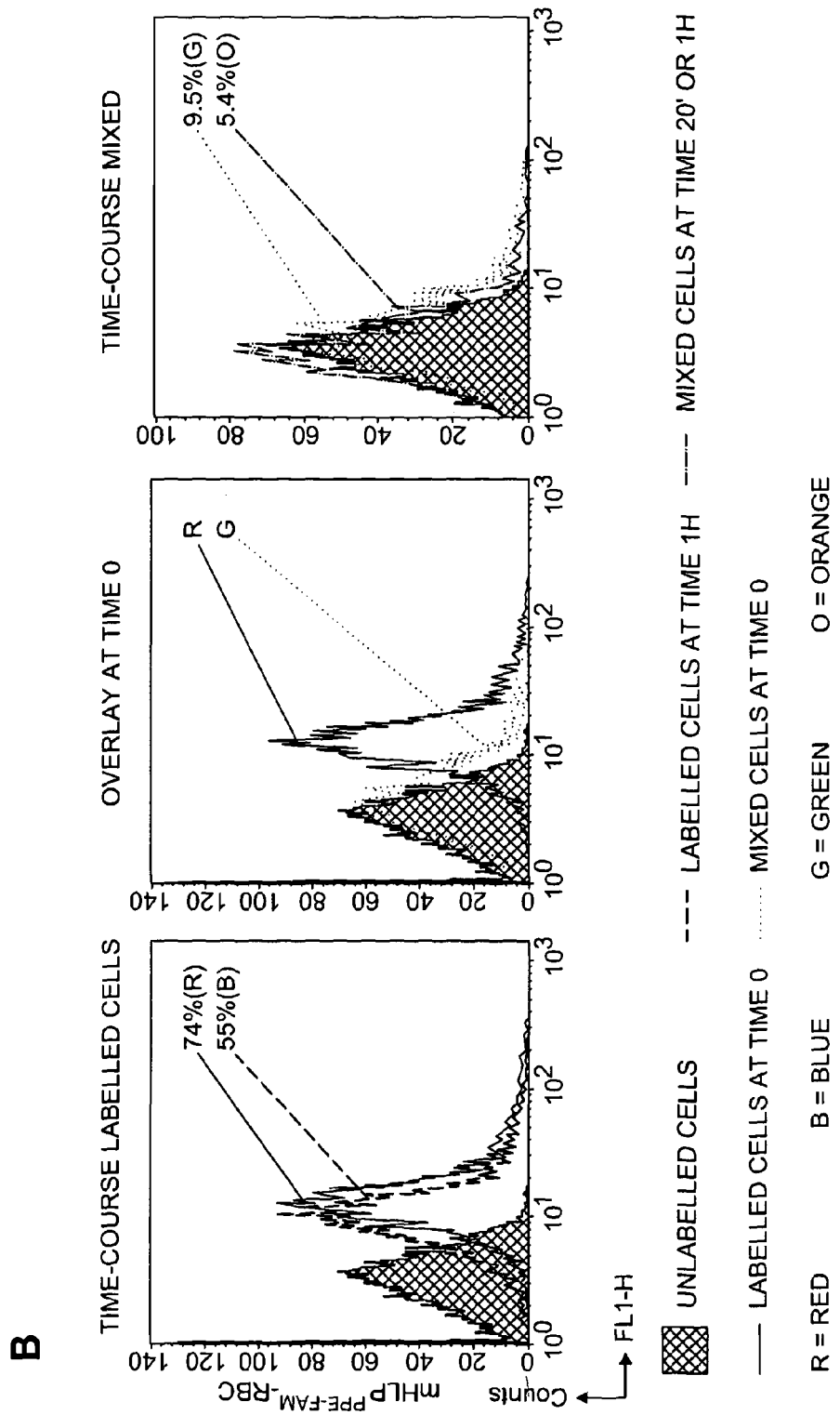

FIG. 4 shows FACS analysis of Compound 5 (identified as mHLP$^{PPE-FAM}$ in the plots) binding to red blood cells (FIG. 4B) and Compound 6 binding to red blood cells (FIG. 4A). In all cases the grey shaded areas show control cell fluorescence. Note that the centre panels in each case are overlays which include the distribution in the left hand panel.

The panels in FIG. 4A show that in the absence of mixing with unlabelled cells (red lines), the cells are efficiently labelled by Compound 6. There was little change in this distribution over 1 hr (blue line). Upon addition of unlabelled cells (green lines), two equal populations were discernable, one labelled and one unlabelled. After 1 h at 25° C. (orange line) this picture remained the same indicating that the two populations remained distinct over this time period and there was no exchange of Compound 6 resulting in a distinct cell population or equilibration of labelled agent resulting in a homogeneous intermediately labelled cell population.

By contrast, the panels in FIG. 4B show that compound 5 behaved differently. The labelling of the cells (red lines, no unlabelled cells added) was less efficient and there some loss of label upon incubation in the absence of unlabelled cells. When these were added (centre panel) even at very early times (time zero is, in practice, a few minutes post-mixing) there was no evidence for two separate cell populations. Instead, a single poorly labelled population (green line) almost coincident with the control distribution was observed. This indicates that Compound 5 (or by inference, Compound 1) was relatively rapidly lost from the surface of red blood cells and probably equilibrated with unlabelled cells by a dissociation/rebinding mechanism. Compound 6 (or by inference, Compound 2) appeared to be much more stably bound and did not undergo equilibration with unlabelled cells by any mechanism, at least over this period of time.

Example 14

Figure 4D:
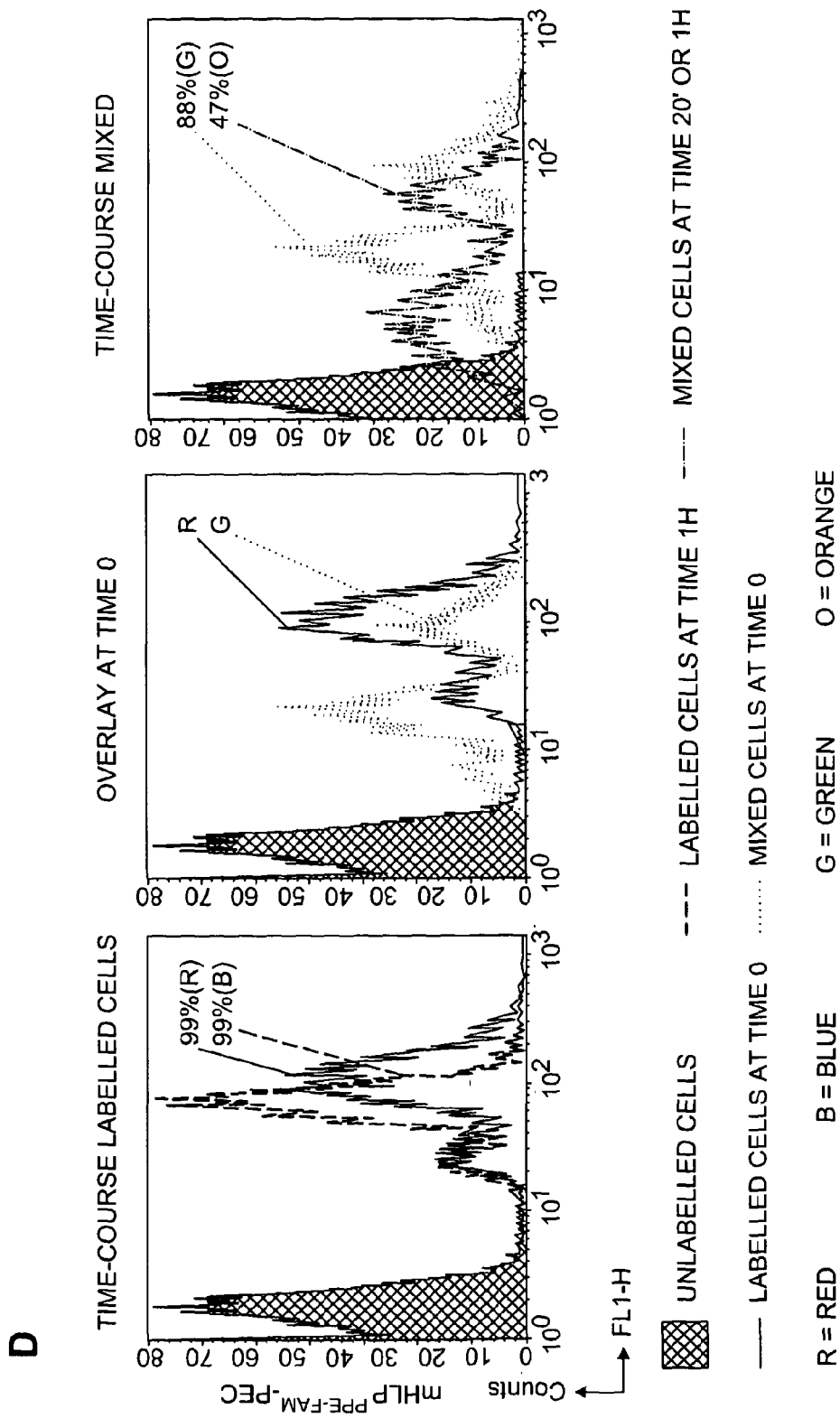

Comparison of the Binding of Compounds 5 and 6 to Porcine Endothelial Cells (FACS) and Measurement of Inter-Cell Transfer FIG. 4 C/D shows results from experiments similar to those described in Example 13 but using PEC cells instead of red blood cells. FIG. 4C (left hand panel) shows that Compound 6 (mHLP$^{bmP-FAM}$) stably labelled two populations of cells in the PEC preparation with different apparent sizes. Upon addition of unlabelled cells (centre and right hand panels), the original two populations remained labelled and as with RBCs, there was no evidence for subsequent equilibration with unlabelled cells. In agreement with the results of Example 13, FIG. 4D showed a lower stability of Compound 5 (mHLP$^{PPE-FAM}$) on PECs and addition of unlabelled cells resulted in a rapid partial equilibration (FIG. 4D centre panel) which, in contrast to the situation with RBCs, was not complete after 1 hour (FIG. 4D right hand panel).

The results of Examples 13 and 14 have implications for the therapeutic uses of the compounds of this invention. For example, Compound 1 appears to undergo quite rapid loss from red blood cells which would render it less suitable for rendering RBCs antithrombotic in blood banking than Compound 2 would be. Both compounds show relatively stable binding to the PEC endothelial cell line but Compound 2 appears to be more stable and hence likely to remain in situ within a perfused organ for longer. These points should be borne in mind when considering the results of Examples 18 and 19 which were obtained with Compound 1.

Example 15

Measurement of Internalisation Rates of Compounds 1 and 2 into Cells Using 2-Colour FACS Analysis of cells using direct single-colour FACS and directly-labelled agents such as Compounds 5 and 6 does not disclose the molecule orientation inside the membrane. To gain insight into internal versus external exposure of the compounds, cells treated with these materials were incubated with an antibody raised against hirudin (anti Hir-mAb) which cross-reacts with the HLL-1 peptide sequence. Compounds located on the outside of cells were detected by FACS using this antibody in combination with a secondary phycoerythrin (PE)-conjugated antibody, at different time points. This system enabled the ratios of externally presented compound (red PE plus green FAM fluorescence) and internalised compound (green fluorescence only) to be estimated.

On RBCs, Compound 2 was initially displayed on outer cell membrane with 82% cells red and green out of a total of 98% labelled cells. After 1 h, the externally detected percentage fell to around 65%. For technical reasons, it was not possible to estimate the same percentages for Compound 5 but when the same experiment was repeated on PEC, the two distinct populations observed previously were again detected. In this case nearly all labelled cells (95% out of 98%) were green and red (indicating external presentation) and their number decreased from 95% to 58% over 1 hour suggesting around 40% internalisation over this period. In the case of Compound 6 on PEC about half of cells (46% out of 98%) were green and red but this ratio did not change with time. It appeared that the cells stably displaying Compound 6 on the outer cell membrane corresponded to the subpopulation characterized previously (see FIG. 4C/D) by smaller size and lower granularity. Further investigations suggested that this subpopulation may have been derived from the PEC parent cells by budding resulting in enucleate "micro-" or "meso" particles. Overall, the internalisation processes for both Compound 5 and 6 did not appear to be rapid. This finding is surprising since it would be expected that the compounds would be internalised relatively quickly.

Example 16

Protocol for a Rat Renal Allograft Model of Hyperacute Transplant Rejection (RATx)

Rat used were inbred male DA (RT1$^a$) and Lewis (RT1$^l$) at the age of 7-8 weeks and a weight of 150-200 g. The model of hyperimmune rejection was based on renal allografts from MHC Class I disparate donors and recipients with modifications to enable life-sustaining renal transplantation. Prior to transplantation, Lewis recipients were pre-sensitised by sequential grafting of three 2×2 cm full thickness skin DA grafts placed to the recipient's dorsal back. The first two skin transplants were received biweekly, followed by a four week period during which alloantibody reached its peak (data not shown), followed by the placement of a third skin graft.

Seven to ten days after the third skin graft, Lewis recipients received a DA kidney graft which had been perfused with different concentrations of Compound 1 (0.1-5 µM) and either flushed or not with Soltran solution (see above).

For the recipient preparation, a midline laparotomy was performed followed by removal of the left kidney. Microaneurysm clips (Johnson & Johnson, UK) were used to clamp the renal vein and artery. The donor kidney was transplanted orthotopically in an end to end anastomosis of the renal vein, artery and ureter using 10-0 sutures (BEAR MEDIC Corp, Japan). The donor and the recipient preparations were taking place simultaneously thus eliminating any cold ischemia. At the end of warm ischemia time, which was 30 minutes, the clips were removed and blood flow was restored to the transplanted kidney. Finally, a second native nephrectomy was performed making the transplanted kidney life-sustaining.

Example 17

Figure 5:
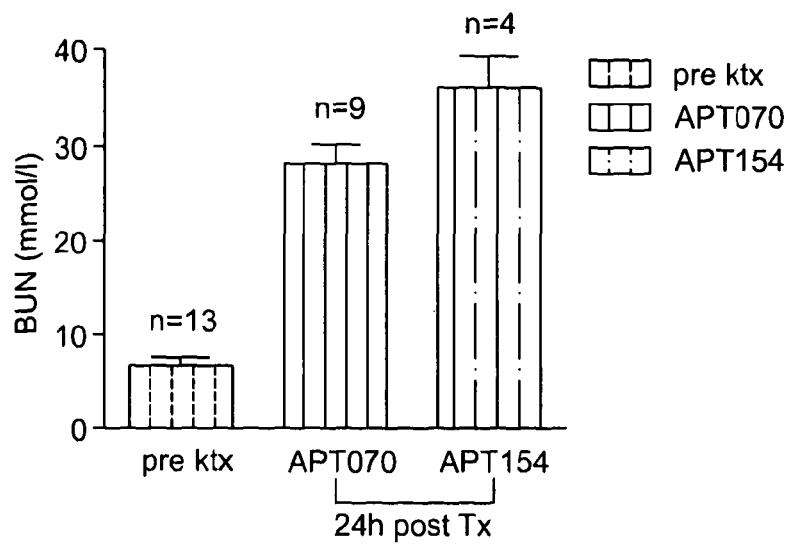
FIG. 5 shows the levels of blood urea nitrogen (BUN) in rats in the RATx model either pre-transplant (red) or treated by local perfusion with 80 ug/ml APT070 (black) or APT154 (blue).

Effects of Control Anti-Complement Agent (APT154) and APT070/Mirococept) in the RATx Model APT070 is a 23 kDa fragment of human complement receptor type 1(CR1) described in WO 98/0245. It contains a membrane-localising tail, MSWP-1, whose structure is the same as that used in Example 4 and which permits it to be administered by perfusion into experimental rat kidneys (Pratt J R et al, *American J. Pathology,* 163, 1457-65, 2003) and into human kidneys (Smith R A G et al, *Molecular Immunology,* 44, 3915, 2007). The retention of APT070 by such organs enables local control of complement activation within the organ. APT154 is the corresponding fragment of CR1 lacking the tail; this agent is not retained by perfused kidneys and therefore acts as control. The inventors assessed the effects of these agents in the RATx model as a preliminary to combination studies with Compound 1. APT070 and APT154 were administered at 80 ug/ml using the perfusion protocol described above. This dose was twice that shown to exert protective effects in a rat model of ischaemia-reperfusion injury not involving anti-donor antibodies generated by pre-sensitisation (Pratt et al, 2003). FIG. 5 shows the levels of blood urea nitrogen (BUN) 24 hrs after transplantation of a donor kidney in the RATx model. There were two kinds of control in this experiment. Animals not subjected to allograft transplantation (pre-ktx group) showed essentially normal BUN levels indicative of normal renal function. Control transplanted animals (APT154 group) had elevated BUN levels typical of severe renal dysfunction. Animals treated with APT070 showed slightly lower BUN levels which were on the borderline of significance. Repeat experiments evaluated 48 h after transplantation showed essentially the same picture (data not shown). Therefore, it appears that a cytotopic anti-complement agent has limited but detectable organ protective effects in this model.

Example 18

Effects of Compound 1 in the RATx Model

In pilot experiments, the donor kidney was perfused with different concentrations (0.1-5 µM) of Compound 1 and left to rest for 10 min before being transplanted. All the concentrations tested resulted in significant bleeding at the site of the anastomosis following transplantation. The threshold concentration for bleeding was around 10 nM. When the same transplants were repeated adding the step of flushing at the end of the intrarenal perfusion (see Example 16), bleeding was reduced to normal for the vessel-incompatible DA and Lewis strains (these strains of rats have different-sized blood vessels). These observations indicated that the excess bleeding was due to unbound Compound 1 delivered systemically to the recipient animal.

Accordingly, further studies were performed by perfusing donor kidneys with 2 uM Compound 1 in approximately 6 ml of Soltran™ perfusion solution and flushing out excess agent.

Figure 6:
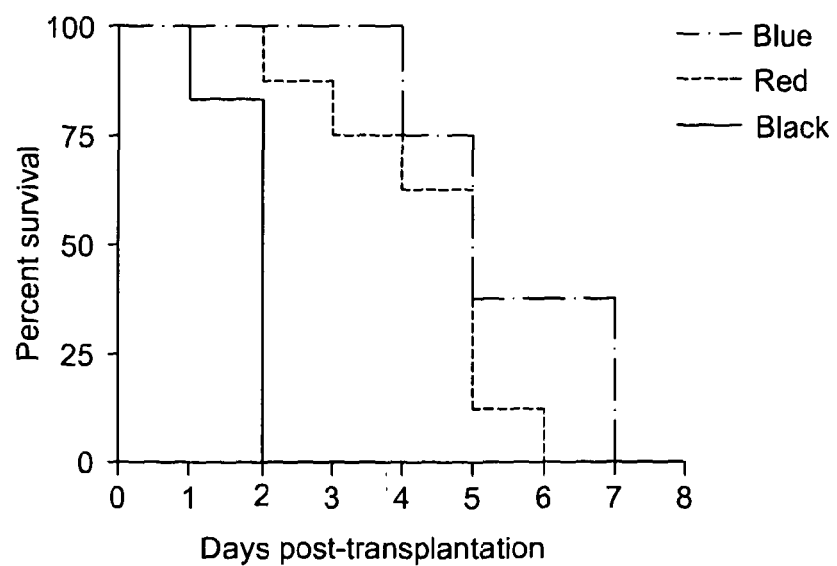
FIG. 6 shows a survival curve (percentage animals alive at a given day post-transplantation) (contol=black; Compound 1 (2 uM)=red; and Compound 1 plus APT070 (2 uM/80 ug/ml)=blue).

FIG. 6 is a Kaplan-Meier survival plot in these animals. Control animals (black line) given Soltran™ perfusion solution did not survive longer than 48 h whereas animals given 2 uM Compound 1 survived 5-6 days (red line). This plots show that the function of the transplanted control kidneys deteriorated rapidly so that within 24 hours all the organs were severely damaged and by 48 hours all had failed completely. Treatment with Compound 1 resulted in prolongation of survival. The prolongation of survival is highly significant given the severity of this model (which has 100% lethality) and the fact that T-cell based immunosuppression was not employed. BUN data (not shown) correlated with survival; deterioration was significantly slower in the treated animals.

Example 19

Effects of Combination Therapy with Mirococept and Compound 1 in the RATx Model FIG. 6 also shows the effect of combining treatment with the complement regulator APT070 and Compound 1 (blue line). Both agents were given together in the same perfusion solution. The plots show that there is an additive effect of the agents on survival with >30% of animals given the combination treatment surviving longer than those receiving Compound 1 alone (red line). APT070 alone had no significant effect on survival (see Example 17). These results indicate firstly that it is feasible to administer both agents together using the perfusion protocol and secondly that the beneficial effect of the agents in this extreme model is at least additive.

---

The invention claimed is:

1. An anticoagulant joined to a joining element, which in turn is joined to a membrane binding element, forming a soluble compound for reducing blood coagulation, wherein the joining element between the anticoagulant and the membrane binding element is less than about 10,000 daltons in weight, and wherein the membrane binding element is a hydrophilic peptide capable of interacting with one or more components of the outer cell membrane, the peptide having between 4 and 20 amino acid residues and comprising between 3 and 8 lysine residues, wherein the peptide additionally comprises a plurality of hydrophobic fatty acyl groups which are capable of interacting with the lipid bilayer core of a cell membrane.

2. The compound of claim 1, wherein the anticoagulant has a weight of less than about 5,000 daltons.

3. The compound of claim 2, wherein the fatty acyl groups are selected from myristoyl and palmitoyl groups.

4. The compound of claim 3, wherein the joining element between the anticoagulant and the membrane binding element is less than about 250 daltons in weight.

5. The compound of claim 4, wherein the membrane binding element comprises N-(α,ε bis-myristoyl lysine) SSKSPSKKDDKKPGD (SEQ ID NO: 3, residues 1-15).

6. The compound of claim 5, wherein the anticoagulant is HLL-1.

7. The compound of claim 1, wherein the anticoagulant is selected from the group consisting of: inhibitors of serine proteases; antagonists of the protease-activated receptors; peptide phosphonates and boronates; hirudin-derived peptides; and arginine/amidinophenylalanine analogues of argatroban and NAPAP.

8. The compound of claim 1, wherein the anticoagulant is an inhibitor of human thrombin (Factor IIa), human Factor Xa, human Factor IXa, human Factor XIa, human Factor XIIa, human kallikrein, human Factor VIIa or human Factor XIIIa.

9. The compound of claim 1, wherein the anticoagulant is HLL-1 or 3-mercaptopropionyl-Phe-Cha-Cha-Arg-Lys-Pro-Asn-Asp-Lys-NH2 (SEQ ID NO. 1).

10. The compound of claim 1, wherein the compound is a conjugate of anticoagulant peptide HLL-1 with 1,2-distearoyl-sn-glycero-3-phosphoethanolamine-N-[2-thiopropionyl(polyethylene glycol)-2000] or a conjugate of anticoagulant peptide HLL-1 with N-(α,ε bis-myristoyl lysine) SSKSPSKKDDKKPGDC-acid (SEQ ID NO. 3).

11. The compound of claim 1, wherein the joining element is less than about 40 amino acids in length.

12. The compound of claim 1, wherein the anticoagulant is less than about 40 amino acids in length from the membrane, when the compound is bound to a membrane.

13. The compound of claim 1 which is in a pharmaceutical composition comprising one or more pharmaceutically acceptable excipients.

14. A method of treatment comprising administering an effective amount of the compound of claim 1 to a subject to reduce blood coagulation.

15. A method of perfusing an organ, tissue or cell comprising contacting the compound of claim 1 with the organ, tissue or cell to reduce blood coagulation.

* * * * *